United States Patent
van de Zande et al.

(10) Patent No.: US 7,736,847 B2
(45) Date of Patent: Jun. 15, 2010

(54) METHODS OF TREATING AND PREVENTING NEUROLOGICAL SYMPTOMS CAUSED BY AVIAN REOVIRUS AND NOVEL ASSOCIATED CHARACTERISTICS

(75) Inventors: Saskia van de Zande, Geel (BE); Rudolf George Hein, Georgetown, DE (US); Donald Eugene Roessler, Bishopville, MD (US); Gwenllyan F. Slacum, Millsboro, DE (US); Karen L. Jensen, Millsboro, DE (US); Phyllis A. Lynch, Laurel, DE (US)

(73) Assignee: Intervet International B.V., Boxmeer (NL)

( * ) Notice: Subject to any disclaimer, the term of this patent is extended or adjusted under 35 U.S.C. 154(b) by 614 days.

(21) Appl. No.: 10/526,706

(22) PCT Filed: Oct. 9, 2003

(86) PCT No.: PCT/US03/31901

§ 371 (c)(1),
(2), (4) Date: Nov. 28, 2007

(87) PCT Pub. No.: WO2004/032959

PCT Pub. Date: Apr. 22, 2004

(65) Prior Publication Data

US 2008/0213304 A1      Sep. 4, 2008

Related U.S. Application Data

(60) Provisional application No. 60/417,245, filed on Oct. 9, 2002, provisional application No. 60/418,586, filed on Oct. 15, 2002, provisional application No. 60/424,163, filed on Nov. 6, 2002, provisional application No. 60/435,192, filed on Dec. 20, 2002.

(51) Int. Cl.
*C12Q 1/70* (2006.01)
*A61K 39/15* (2006.01)

(52) U.S. Cl. .................................. 435/5; 424/215.1

(58) Field of Classification Search .................. None
See application file for complete search history.

(56) References Cited

U.S. PATENT DOCUMENTS

| 5,162,369 | A | 11/1992 | Ashmead et al. |
| 5,525,342 | A | 6/1996 | Rosenberger et al. |
| 6,951,650 | B1 * | 10/2005 | van Loon .............. 424/215.1 |

OTHER PUBLICATIONS

91st Annual Meeting Abstracts hosted by the University of Delaware, Aug. 11-14, Poscal 80 (Supplement 1), 2002, p. 160.
Drastini et al. Journal of Virological Methods 39:269-278 (1992).
Estes, et al. American Journal Veterinary Research, 41:1 pp. 151-152 (1980).
Green et al. Journal of Virology, 62:5 pp. 1819-1823 (1988).
Kang et al. Journal of Clinical Microbiology, 31:9 pp. 2291-2296. (1993).
Virus Infections of Birds, J.B. McFerran and M.S. McNulty, eds., in vol. 4 of Virus Infections of Vertebrates, Elsevier Science Publishers B.V. pp. 177-179 and 181-190 (1993).
Nwajei et al. Avian Pathology 17:759-766, (1988).
Rekik et al. Avian Diseases, 36:237-246 (1992).
Van de Zande et al. Veterinary Microbiology 120:42-49 (2007).
Wood et al. Journal of Comparative Pathology, 90:29-38 (1980).
PCT Internation Search Report of International application No. PCT/US2003/31901, International filing date Oct. 9, 2003, 5 pages.
Rekik et al. Avian Pathology 20:607-617 (1991).

* cited by examiner

*Primary Examiner*—Stacy B Chen
(74) *Attorney, Agent, or Firm*—William M. Blackstone; William P. Ramey, III

(57) ABSTRACT

Embodiments of the present invention generally relate to novel methods for the treatment and/or prevention of neurological symptoms caused by an avian reovirus, enteric reovirus strain (ERS), and associated characteristics. Other embodiments generally comprise an immunogenic composition or vaccine comprising an ERS for the treatment and/or prevention of neurological symptoms.

5 Claims, No Drawings

METHODS OF TREATING AND PREVENTING NEUROLOGICAL SYMPTOMS CAUSED BY AVIAN REOVIRUS AND NOVEL ASSOCIATED CHARACTERISTICS

RELATED APPLICATIONS

This application claims priority from provisional application No. 60/417,245, filed on Oct. 9, 2002, provisional application No. 60/418,589, filed on Oct. 15, 2002, provisional application No. 60/424,163, filed on Nov. 6, 2002, and provisional application No. 60/435,192, filed on Dec. 20, 2002.

FIELD OF THE INVENTION

The present invention is related to methods of treating and/or preventing neurological symptoms caused by avian reovirus and novel associated characteristics.

BACKGROUND OF THE INVENTION

Reovirus infections are prevalent worldwide in poultry and have been isolated from chickens showing a wide variety of clinical signs including viral arthritis/tenosynovitis, malabsorption syndrome (MAS), pericarditis, myocarditis, and immunosuppression [McNulty et al., "Virus infection of birds," Reovirus, Chapter 13, pp 181-193 (1993)].

Viral arthritis/tenosynovitis particularly in broiler breeds is the most important disease attributable to reovirus infection. [Nibert et al., Fields Virology 4: p. 1681 (2001)]. It is a persistent viral infection with chronic inflammatory lesions, confined mainly to the hock joints and leg tendons of the chicken. The lesions are localized to synovial structures [Menendez et al., Avian Dis. 19: 112-117 (1975); Ellis et al, Avian Dis. 27: 644-651 (1983); Kibenge et al, Avian Pathol. 14: 87-98 (1985)]; [Nibert et al., Fields Virology 4: p. 1681-1682 (2001)].

Clinical signs/symptoms of reovirus infection have also been associated with malabsorption syndrome (MAS) by several groups [Kouwenhoven et al., Avian Pathol. 7: 183-187 (1978); Page et al., Avian Dis. 26:618-624 (1982); Hieronymus et al., Avian Dis. 27: 255-260 (1983); Goodwin et al, Avian Dis. 37: 451-458 (1993)]. The syndrome is characterized by weight gain depression with non-uniform growth, defective feathering and diarrhea with undigested food and watery content. The pathologic changes mostly include proventriculitis enteritis, pancreatitis and hepatitis. MAS may be caused either by maldigestion or malabsorption or both. Lesions that are found can cause an impairment of digestion by insufficiency of digestive secretions and or an impairment of absorption because of insufficient absorptive capacity. However, there are a variety of pathogenicities of reovirus isolated from MAS as can been seen in the variations of depressed weight gains. [Nibert et al., Fields Virology 4: p. 1681-1682 (2001); Page et al., Avian Dis. 26:618-624 (1982); McNulty et al., Avian Pathol. 13: 429-439 (1984); Decaesstecker et al., Avian Pathol. 15: 769-782 (1986); Kibenge and Dhillon, Avian Dis. 31: 39-42 (1987); Kouwenhoven et al., Avian Pathol. 17: 879-892 (1988); Montgomery et al., Avian Dis. 41: 80-92 (1997) Songserm et al., Avian Dis. 46: 87-94 (2002)]. To date, there has been no disclosure in the prior art of an avian reovirus causing neurological symptoms.

There are several prior art vaccines for known avian reoviruses. Examples of live vaccines include strain S1133 and 2177. Live vaccines in the United States have been developed from various passage levels of avian reovirus strain S1133, isolated and characterized by van der Heide from a field case of tenosynovitis. Strain S1133 was grown serially 235 times in the chorioallantoic membrane (CAM) at 37.degree. C. and then 65 times in chicken embryo fibroblast (CEF) at 32.degree. C. An additional 135 passages were carried out at 37° C. in CEF [van der Heide et al., Avian Dis., 27:698-706 (1983)]. Strain 2177 was isolated and characterized by Rosenberger from a field case of avian reovirus [U.S. Pat. No. 5,525,342]. Strain 2177 was isolated from chickens exhibiting reovirus disease by inoculating tissue samples into embryonated eggs and collecting the yolk fluid. This yolk fluid was then inoculated into CEF and passed 14 times until the cytopathology was observed at which time the virus was plaque purified. This yolk fluid was then propagated in embryonated eggs to produce a stock of virus. The stock was found to be non-pathogenic and was titled strain 2177. To date, no reovirus has been able to be grown/cultured immediately upon Vero cells without adaptation. [Nibert et al., Fields Virology 4: pp. 1681-1682 (2001)]. The most common method is propagation in embryonated chicken eggs. There is disclosure in the prior art of an orthoreovirus from an Australian flying fox, a mammalian reovirus, having some characteristics of an avian orthreovirus (reovirus) that is able to be propagated in mammalian cells. [Nibert et al., Fields Virology 4: p. 1682 (2001)]. However, there is no disclosure in the prior art of an avian reovirus that is able to be propogated in a mammalian cell without adaptation. [Nibert et al., Fields Virology 4: p. 1682 (2001)]. As well, the prior art does not disclose a method of treating and/or preventing neurological symptoms in poultry caused by an avian reovirus. Accordingly, the art field is in search of a method to treat and/or prevent neurological symptoms cause by an avian reovirus.

Recently, van Loon et al [Veterinary Quarterly, 23: 129-133 (2001)] described the isolation and identification of a new class of reoviruses, the so-called enteric reovirus strains (ERS). ERS was isolated from broilers in showing high mortality. Those broilers came from parent flocks that were well vaccinated against reovirus infections. It became clear that ERS was a new serotype of reovirus since the virus could not be neutralized by known reoviruses using the plaque reduction test [van Loon et al., Veterinary Quarterly, 23: 129-133 (2001)]. Furthermore, characterization of ERS with a panel of monoclonal antibodies revealed that these strains showed a distinct panel pattern compared to reovirus strains that have been described in the literature previously [Hieronymus et al., Avian Dis. 27: 246-254 (1983); Johnson, Avian Dis. 16: 1067-1072 (1972); Olson et al., Am J Vet Res. 18: 735-739 (1957); Rosenberger et al, Avian Dis. 33: 535-544 (1989); van der Heide et al., Avian Dis. 18: 289-296 (1974)]. The novel antigenic class of reovirus was further identified by the art-accepted practice of a plaque reduction assay, U.S. patent application No. An explanation of a plaque reduction assay may be found in an article by Nersessian et al. (J. Vet. Res. N50, 1989, pp. 1475-1480). The article confirms the heterogenic immunological character of avian reovirus and validates the use of plaque reduction assays for determining and characterizing antigenic relationships (including, but not limited to, similarities and differences) between reovirus isolates. Upon screening for Reoviruses in the field, it was observed that ERS type strains were also present in The Netherlands, Belgium, Ireland, United Kingdom, Spain, Germany, Italy, USA, Argentina, United Arabic Emirates, South Africa, The Philippines and Indonesia. These ERS type strains were usually isolated from birds with MAS. Studies of the pathogenicity and dissemination of ERS in specific pathogen free (SPF) chickens demonstrated that ERS was able to induce a high mortality, tenosynovitis (unpublished observations) and MAS [van Loon et al., Veterinary Quarterly, 23:

129-133 (2001)]. Also in commercial broilers with maternally derived antibodies against reovirus, van Loon et al [Veterinary Quarterly, 23: 129-133 (2001)] showed a growth retardation of respectively 35% and 25% in broilers inoculated at day old or at 7 days old. Further study and evaluation of this novel class has yielded other surprising characteristics.

SUMMARY OF THE INVENTION

Generally, embodiments of the present invention relate to a class of avian reovirus that causes neurological symptoms and methods of treating and/or preventing neurological symptoms caused by the class of avian reovirus.

In an embodiment, it has been discovered that the class of reovirus referred to as avian Enteric Reovirus Strain (ERS) causes neurological symptoms. Such neurological symptoms comprise, but are not necessarily limited to, twisted neck, tremors, and/or the like. Further, it has been discovered, in an embodiment, that a method of treating and/or preventing neurological symptoms caused by an avian reovirus comprises administering an effective amount of an immunogenic composition or vaccine comprising an ERS avian reovirus in a live, attenuated or killed form and a carrier or diluent.

In an embodiment of a method of the present invention, the immunogenic composition or vaccine administered comprises reoviruses of an antigenic class of reovirsuses defined as having the characteristics of embodiments of the class of virus of U.S. application Ser. No. 09/493,484 (hereinafter referred to as the '484 application). The '484 application claims priority from published European Patent application number 00200256.6, filed on Jan. 25, 2000. The European Patent application published on Aug. 2, 2000 under publication number EP 1 024 189 A1.

Such class of reovirus is defined as belonging to the class of reovirus that is able to induce antiserum in an animal, which antiserum causes a reduction of the plaques formed by strain ERS, a sample of which is deposited at the ECACC, Salisbury, UK, under accession no. 99011475, of at least 75% in a plaque reduction assay, and, such class is further defined by reactivity in an IFT with a polyclonal antiserum raised against an avian reovirus isolate, preferably against the prototype reovirus strain 1133, and the absence of reactivity in the IFT with the Moabs INT 13-06, INT 14-11 and 15-01 INT (hybridomas of which are deposited at the ECACC under accession no. 99011472, 99011473 and 99011474, respectively).

Nothing in this summary should be construed as limiting the scope of the invention. For a further understanding of the scope of invention, attention should be had to the following detailed description, examples and claims.

DETAILED DESCRIPTION OF THE INVENTION

As used herein, the term "relatively non-pathogenic" means and refers to a significant reduction in the pathology of a virus, such that less than or equal to about 20% of poultry immunized with a live strain of the virus would be affected by the virus. As used herein, the term "chicken" means and refers to all chickens, including broilers, reproduction stock, laying stock and the like. The term "poultry," includes, but is not limited to, chickens, turkeys, water fowl, guineas, quail, pigeons, ostriches, and the like. As used herein, the term "naturally" means without human intervention. However, it is contemplated that a "naturally non-pathogenic" strain may be passaged in various embodiments to prepare a virus stock and the like. It is further contemplated that such passaging does not cause a virus to be considered other than "naturally non-pathogenic" if the virus was "relatively non-pathogenic," as defined, before passaging.

As used herein, the term "vaccine strain" means and refers to a viral strain suitable for use in an immunogenic composition or vaccine. A "vaccine strain" can comprise, but is not necessarily limited to, a non-pathogenic strain or relatively non-pathogenic strain, a killed strain, and/or an attenuated strain.

The '484 application, filed on Jan. 28, 2000 defined, for the first time, a novel antigenic class of avian reovirus. The '484 application claims priority from published European Patent application number 00200256.6, filed on Jan. 25, 2000. The European Patent application published on Aug. 2, 2000 under publication number EP 1 024 189 A1.

The novel class in the application was characterized as avian reovirus ERS (enteric reovirus strain). The class was identified as ERS because the class was found to cause enteric disorders, a reovirus associated disease, such as too liquid feces and/or maldigested food. Now, surprisingly, it has been found that the class of reovirus, the avian reovirus ERS, causes neurological symptoms. The neurological symptoms include, but are not limited to, nor require all, twisted neck (also referred to as torticollosis) and tremors.

Accordingly, embodiments of the present invention generally relate to a class of avian reovirus that causes neurological symptoms and methods for preventing neurological symptoms caused by an avian reovirus. In an embodiment, methods of the present invention comprise administering an effective amount of an immunogenic composition or vaccine comprising an avian reovirus that causes neurological symptoms in a live, attenuated or killed form and a carrier or diluent. Therefore, further embodiments are directed towards an immunogenic composition or vaccine comprising reovirus of an antigenic class of reovirsuses having the characteristics of the class of virus of European Application EP 1 024 189 A1.

Such class of reovirus is defined as belonging to the class of reovirus that is able to induce antiserum in an animal, which antiserum causes a reduction of the plaques (plaque reduction assay) formed by strain ERS, a sample of which is deposited at the ECACC, Salisbury, UK, under accession no. 99011475, of at least 75% in a plaque reduction assay, and/or, such class is further defined by reactivity in an IFT with a polyclonal antiserum raised against an avian reovirus isolate, preferably against the prototype reovirus strain 1133, and the absence of reactivity in the IFT with the Moabs INT 13-06, INT 14-11 and 15-01 INT (hybridomas of which are deposited at the ECACC under accession no. 99011472, 99011473 and 99011474, respectively).

Other reovirsues of the present invention and for use in vaccines/methods of the present invention are characterized in that the reovirus of the immunogenic composition or vaccine that belongs to the class of reovirus that is able to induce antiserum in an animal, which antiserum causes a reduction of the plaques formed by strain ERS of at least 80% in a plaque reduction assay. Other reoviruses of the present invention and for use in vaccines/methods of the present invention are characterized in that the reovirus of the immunogenic composition or vaccine that belongs to the class of reovirus that is able to induce antiserum in an animal, which antiserum causes a reduction of the plaques formed by strain ERS of at least 90% in a plaque reduction assay.

Exemplary, non-limiting, strains representative of reoviruses suitable for use in methods of the present invention include, but are not limited to, strain ERS (isolate 1), deposited at the ECACC, Salisbury, UK, under accession no. 99011475; strain ERS 1037, deposited at the ATCC, Manassas, Va. 20108, U.S.A. on Oct. 1, 2002, under accession no. pta-4735; strain ERS 060E, deposited at the ATCC, Manassas, Va. 20108, U.S.A. on Oct. 30, 2002, under accession no. pta-4782; and, strain ERS 074, deposited at the ATCC, Manassas, Va. 20108, U.S.A. on Oct. 30, 2002, under accession no. PTA-4783.

Strains of the present invention and strains used in immunogenic compositions or vaccines for methods of the present invention may be isolated from poultry as is common in the art. For chickens, a strain of reovirus is isolated from chickens with reovirus associated disease. Processes for virus isolation are common in the art. In an isolation, the virus was isolated from infected tendons collected from broilers showing signs of reovirus associated disease. However, methods of the present invention are not limited by from what part of avian the virus is isolated.

In fact, surprisingly, it has been found that avian reovirus of the present invention may be isolated from the neurological system of poultry suffering from avian reovirus induced neurological symptoms, such as from the brain and the spinal chord. Avian reovirus has not previously been isolated from the brain, spinal chord, and/or other structures associated with the neurological system. Further, it is believed that only strains causing neurological symptoms may be isolated from the brain, spinal chord, and/or other structures associated with the neurological system. In fact, it is illustrated in the Experimental section that prior art reoviruses not causing neurological symptoms cannot be isolated from the brain, spinal chord, and/or other structures associated with the neurological system.

Accordingly, the present invention discloses a class of avian reoviruses that may be isolated from the neurological system of poultry. In various embodiments, the class of avian reovirus so characterized may be isolated from the brain, spinal chord, and/or other structures associated with the neurological system.

In various embodiments, immunogenic compositions or vaccines used with methods of the present invention may be administered alone or in combination with other viral vaccines for poultry, such as those for Marek's Disease Virus, Infectious Bursal Disease Virus, Newcastle Disease Virus, Infectious Bronchitis Virus, Avian Encephalomyelitis Virus, Fowl Pox Virus, Chicken Anemia Agent and/or the like. Other embodiments may combine bacterial antigens and the like. Further, preferred immunogenic compositions or vaccines used with methods of the present invention are vaccines which may be administered at a young age (e.g., one day) and/or in vivo.

Administration of immunogenic compositions or vaccines in methods of the present invention may be by any route commonly used for avian reovirus administration Preferred routes of administration include mass application routes, such as drinking water (orally) and spray. However, other embodiments of administration may include injection and the like.

It is common in administration by the drinking water route to deprive the animals of water for about 2 to 4 hours before placing the immunogenic composition or vaccine containing water before them. It is important that there is enough drinker space for all birds to drink evenly to allow for even vaccine dispersion. The vaccine is applied in fresh drinking water at an effective amount, a concentration calculated to give each bird a sufficient dose for an immunogenic composition or vaccine.

In various embodiments, in order to prevent a reduction of the viable vaccine virus by the presence of small amounts of chlorine, iron, zinc or copper ions in the drinking water and/or to prevent inactivation of the live vaccine virus because of increased concentration of dissolved salts as a result of desiccation of the drinking water, small amounts of a protein protectant, such as skimmed milk, skimmed milk powder or gelatin can be added to aqueous phase.

In various embodiments utilizing a spray method, common methods of application include, but are not limited to, a coarse spray application and an aerosol administration. In the coarse spray method particles usually have an initial droplet size ranging from 10 to 100 microns and in the aerosol administration method droplets usually range from $<1$ to 50 microns. However, any droplet size may be used in varying embodiments of the invention.

It is common in the industry to utilize conventional spray-apparatus and aerosol generators for the generation of the small particles, such as the commercially available spray generators for knapsack spray, hatchery spray and atomist spray. Details concerning conventional spray/aerosol- and drinking water vaccination can be found in the "Compendium, administration of poultry vaccines" issued by the Gezondheidsdienst voor Pluimvee, Doom, The Netherlands, van Eck et al., VI-VII, 1988.

Further embodiments of a method of the present invention may utilize administration of a vaccine through eye drop and/or beak dipping and/or any other method(s) common in the art.

Other embodiments of the present invention may utilize administration of an inactivated avian reovirus. Inactivated forms potentially provide a benefit of elevated levels of protective antibodies for a long duration. This property makes an inactivated vaccine particularly well suited for breeder vaccination, in certain instances.

As is known in the art, an aim in the inactivation of viruses harvested after propagation is to eliminate reproduction of viruses. In general, this can be achieved by chemical or physical means. Chemical inactivation can be effected by treating the viruses with, for example, enzymes, formaldehyde, β-propiolactone, ethylene-imine, or a derivative thereof. If necessary, the inactivating material is neutralized afterwards. For example, material inactivated with formaldehyde can be neutralized with thiosulphate. Physical inactivation can preferably be carried out by subjecting the viruses to energy-rich radiation, such as UV light or γ-rays. If desired, after treatment the pH can be adjusted to a value of about 7.

Inactivated vaccines may be administered parent rally, e.g. intramuscularly, subcutaneously, or any other method common in the art.

While the invention has been described in connection with specific embodiments thereof, it will be understood that it is capable of further modifications and the appended Claims are intended to cover any variations, uses, or adaptations of the invention following, in general, the principles of the invention and including such departures from the present disclosure as come within known or customary practice within the art to which the invention pertains and as may be applied to the essential features hereinbefore set forth whether now existing or after arising. Further, while embodiments of the invention have been described with specific dimensional characteristics and/or measurements, it will be understood that the embodiments are capable of different dimensional characteristics and/or measurements without departing from the principles of the invention and the appended Claims are intended to cover such differences. Furthermore, all patents, patent applications, articles, and other publications mentioned herein are herby incorporated by reference.

For a further understanding of various embodiments of the present invention, reference should be had to the following examples:

EXAMPLES

Samples from flocks of chickens in the United States of America were taken and isolated into strains. Certain of these strains were identified as ERS 060E, ERS 074, and ERS 1037. The flocks from which these chickens were taken were experiencing classic symptoms of ERS, including, but not limited to enteritis. Serum from certain chickens was sent to Boxmeer, The Netherlands for a panel pattern to confirm that the chickens belonged to the antigenic class identified in EP 1 024 189 A1. All three sera illustrated the absence of reactivity in an IFT with Moabs INT 13-06, INT 14-11, and 15-01 INT.

Based upon the results comprising the study, it was determined that strains ERS 1037, ERS 060E, and ERS 074 belonged to the novel antigenic class of reoviruses identified as ERS in EP 1 024 189 A1.

Further studies of strains ERS, ERS 060E and ERS 074 revealed that the novel antigenic class of reoviruses causes neurological symptoms in infected poultry. Such neurological symptoms including, but not limited to twisted neck, tremors and/or the like. The observations were made in both SPF chickens and commercial broilers, with maternally derived antibodies against reovirus, after infection with the novel antigenic class of reovirus, ERS.

In one example, when chickens were inoculated via the foot pad route and/or subcutaneous at one day old, the survivors developed nervous symptoms such as tremors and twisted neck. These symptoms can be seen after inoculation.

In the field, ERS was isolated from chickens showing neurological symptoms. These neurological symptoms could be reproduced under experimental conditions with the isolated ERS strain.

Example 1

Ongoing studies have revealed that strains of avian reovirus causing neurological symptoms can be isolated from the brain and/or spinal chord.

In one example, ERS 074 was reisolated from SPF Chickens' brains and spinal chords using the following procedure:

1. Chickens showing neurological symptoms were necropsied and the head and necks were collected and frozen. A chicken was determined to be showing neurological symptoms when the chicken was observed with twisted neck and/or tremors.

2. Heads and necks were thawed.

3. Brain and upper portion of the spinal cord were aseptically swabbed.

4. Swabs were placed in TPB and vortexed.

5. Samples were frozen/thawed three times.

6. Samples ere centrifuged for 10 minutes at approx. 3000 rpm.

7. Supernatant was removed and filtered through 0.45 μm and 0.2 μm syringe filters.

8. 0.1 ml of filtered material was inoculated into 10 day eggs using the drop CAM route.

9. Eggs were candled daily for death.

10. Six days post inoculation all eggs were opened.

11. Liver and chorioallantoic membranes were harvested from infected embryos.

12. Liver and chorioallantoic membranes were homogenized using a Waring blender.

13. Homogenates were frozen and thawed three times.

14. An AGP (Agar Gel Precipitin Test) was used to detect avian reovirus antigen.

The AGP test was positive for avian reovirus antigen.

Example 2

Panel Pattern

Polyclonal antiserum was prepared by infecting rabbits (1-1.5 kg) with purified avian reovirus strain 1133. Booster injections took place 28 and 84 days after the first injection. Blood was collected and serum isolated 14 days after the last injection.

Different reovirus were characterized with different Moabs. In an embodiment, primary CEL cells were grown in 96-well polystyrene microtitre plates. Uninfected cells served as controls. After 2-4 days of incubation at 37° C. with 5% $CO_2$, infected monolayers were fixed with cold 96% ethanol. The alcohol was discarded and the plates were washed with washing buffer and 100 μl of different hybridoma cell culture supernatant diluted 1:50 or 1:200 in PBS or 100 μl of rabbit polyclonal serum (rabbit 68A) diluted 1:50, was added to each well. The plates were incubated for 60-90 minutes at 37° C., washed twice with washing buffer and reacted with 1:100 diluted fluorescent isothiocyanate-labelled rabbit anti-mouse or 1:100 diluted isothiocyanate-labelled goat anti-rabbit serum. The plates were then washed and fixed with a glycerol/PBS solution (1:1). The presence of fluorescence was observed with a fluorescence microscope.

The antiserum panel used in this experiment consisted of the following polyclonal antiserum and Moabs raised against the prototype avian reovirus strain 1133:

| | |
|---|---|
| Rabbit 68A | rabbit polyclonal antiserum |
| Moab 154 | Vakharia et al. 1996 (supra) |
| Moab 14-67 | Intervet International B.V. |
| Moab INT 13-06 | ECACC accession no. 99011472* |
| Moab INT 14-11 | ECACC accession no. 99011473* |
| Moab 15-01 INT | ECACC accession no. 99011474* |

The panel pattern was as follows:

| Strain | Rabbit 68A | 154 | 14-67 | 14-11 | 13-06 | 15-01 |
|---|---|---|---|---|---|---|
| S-1133 | + | + | + | + | + | + |
| 2408 | + | + | + | + | + | + |
| 1733 | + | + | + | + | + | + |
| 2177 | + | + | + | - | - | + |
| ERS$_{(isolate\ 1)}$ | + | + | + | - | - | - |
| ERS 1037 | + | + | + | - | - | - |
| ERS 060E | + | + | + | - | - | - |
| ERS 074 | + | + | + | - | - | - |
| ERS 015 | + | + | + | - | - | - |

*hybridomas of the Moabs arte deposited

As can be seen from the panel patterns, strains ERS 1037, ERS 060E, and ERS 074 have a comparable pattern to strain ERS (isolate 1) while being differentiated from strains S-1133, 2408, 1733, and 2177.

Example 3

The following experiments demonstrate studies conducted with various identified strains.

Experiment 3a

Experimental Design

Twenty SPF chickens were inoculated orally at day old with 0.5 ml plaque purified strain ERS (isolate 1) (6.09 $\log_{10}TCID_{50}$/bird). The chickens were observed daily for clinical sign during 14 days. At 14 days of age all chickens were slaughtered.

Results

35% of the chickens died during the first 6 days (Table 1). At day 10, one chicken developed neurological symptoms and at day 13 a second chicken showed neurological symptoms. Further, chicks infected with ERS demonstrated a 10.1 gram/day weight gain, while the control group experienced a 17.0 gram/day weight gain.

TABLE 1

Percentage mortality

| Days after inoculation | Mortality (number birds) | % Mortality |
|---|---|---|
| 3 | 1 | 5 |
| 4 | 2 | 15 |
| 5 | 3 | 30 |
| 6 | 1 | 35 |

TABLE 2

Percentage neurological symptoms

| Days after inoculation | Neurological Symptoms (number birds/remaining birds)* | % NS |
|---|---|---|
| 10 | 1/13 | 7.7 |
| 13 | 1/13 | 15 |

*A chicken was determined to be showing neurological symptoms when the chicken was observed with twisted neck and/or tremors.

Experiment 3b

10 SPF chickens were inoculated subcutaneously with 0.2 ml at one day of age with strain ERS 060E ($10^3$ $TCID_{50}$/bird): The chickens were observed for clinical sign at 15 days.

TABLE 1

Percentage mortality

| Days after inoculation | Mortality (no. of birds) | % Mortality |
|---|---|---|
| 20 | 2 | 20 |

TABLE 2

Percentage neurological symptoms

| Days after inoculation | Neurological Symptoms (number birds)* | % NS |
|---|---|---|
| 20 | 4 | 40 |

*A chicken was determined to be showing neurological symptoms when the chicken was observed with twisted neck and/or tremors.

Results.

20% of the birds died during the first 15 days. 40% of the birds suffered from neurological symptoms. Further, chicks infected with ERS 060E demonstrated an average 93.82 gram/day weight gain.

Experiment 3c

10 SPF chickens were inoculated subcutaneously with 0.2 ml at one day of age with strain ERS 074 ($10^3$ $TCID_{50}$/bird). The chickens were observed for clinical sign at 20 days.

TABLE 1

Percentage mortality

| Days after inoculation | Mortality (no. of birds) | % Mortality |
|---|---|---|
| 20 | 3 | 30 |

TABLE 2

Percentage neurological symptoms

| Days after inoculation | Neurological Symptoms (number birds)* | % NS |
|---|---|---|
| 20 | 0 | 0 |

*A chicken was determined to be showing neurological symptoms when the chicken was observed with twisted neck and/or tremors.

Results:

30% of the birds died during the first 20 days. 0.0% of the birds suffered from neurological symptoms. Further, chicks infected with ERS 074 demonstrated a 126.38 gram/day weight gain.

Experiment 3d

10 SPF chickens were inoculated via the foot pad route with 0.2 ml at one day of age with strain ERS 060E ($10^3$ $TCID_{50}$/bird). The chickens were observed for clinical sign at 20 days.

TABLE 1

Percentage mortality

| Days after inoculation | Mortality (no. of birds) | % Mortality |
|---|---|---|
| 20 | 2 | 20 |

TABLE 2

Percentage neurological symptoms

| Days after inoculation | Neurological Symptoms (number birds) | % NS |
|---|---|---|
| 20 | 1 | 10 |

*A chicken was determined to be showing neurological symptoms when the chicken was observed with twisted neck and/or tremors.

Results:

20% of the birds died during the first 20 days. 10% of the birds suffered from neurological symptoms. Further, chicks infected with 060E demonstrated a 87.81 gram/day weight gain.

Experiment 3e

10 SPF chickens were inoculated via the foot pad route with 0.2 ml at one day of age with strain ERS 074 ($10^3$ TCID$_{50}$/bird). The chickens were observed for clinical sign at 20 days.

TABLE 1

Percentage mortality

| Days after inoculation | Mortality (no. of birds) | % Mortality |
|---|---|---|
| 20 | 10 | 100 |

TABLE 2

Percentage neurological symptoms

| Days after inoculation | Neurological Symptoms (number birds)* | % NS |
|---|---|---|
| 20 | 5 | 50 |

*A chicken was determined to be showing neurological symptoms when the chicken was observed with twisted neck and/or tremors.

Results:

100% of the birds died during the first 20 days. 50% of the birds suffered from neurological symptoms. Further, chicks infected with ERS 074 demonstrated a 94.37 gram/day weight gain.

Experiment 3f 20 broiler chickens were inoculated subcutaneously with 0.2 ml at one day of age with strain ERS 060E ($10^3$ TCID$_{50}$/bird). The chickens were observed for clinical sign at 14 days.

TABLE 1

Percentage mortality

| Days after inoculation | Mortality (no. of birds) | % Mortality |
|---|---|---|
| 14 | 3 | 15 |

TABLE 2

Percentage neurological symptoms

| Days after inoculation | Neurological Symptoms (number birds)* | % NS |
|---|---|---|
| 14 | 2 | 10 |

*A chicken was determined to be showing neurological symptoms when the chicken was observed with twisted neck and/or tremors.

Results:

15% of the birds died during the first 14 days. 10% of the birds suffered from neurological symptoms. Further, chicks infected with ERS 060E demonstrated an average weight of 543 grams at 21 days post-inoculation. Negative control birds had an average weight of 751 grams at 21 days post-inoculation.

Experiment 3g 20 broiler chickens were inoculated subcutaneously with 0.2 ml at one day of age with strain ERS 074 ($10^3$ TCID$_{50}$/bird). The chickens were observed for clinical sign at 14 days.

TABLE 1

Percentage mortality

| Days after inoculation | Mortality (no. of birds) | % Mortality |
|---|---|---|
| 14 | 5 | 25 |

TABLE 2

Percentage neurological symptoms

| Days after inoculation | Neurological Symptoms (number birds)* | % NS |
|---|---|---|
| 14 | 5 | 25 |

*A chicken was determined to be showing neurological symptoms when the chicken was observed with twisted neck and/or tremors.

Results:

25% of the birds died during the first 14 days. 25% of the birds suffered from neurological symptoms. Further, chicks infected with ERS 074 demonstrated an average weight of 488 grams at 21 days post-inoculation. Negative control birds had an average weight of 751 grams at 21 days post-inoculation.

Experiment 3h 20 broiler chickens were inoculated via the foot pad route with 0.2 ml at one day of age with strain ERS 060E ($10^2$ TCID$_{50}$/bird). The chickens were observed for clinical sign at 14 days.

TABLE 1

Percentage mortality

| Days after inoculation | Mortality (no. of birds) | % Mortality |
|---|---|---|
| 14 | 5 | 25 |

TABLE 2

Percentage neurological symptoms

| Days after inoculation | Neurological Symptoms (number birds)* | % NS |
|---|---|---|
| 14 | 1 | 5 |

*A chicken was determined to be showing neurological symptoms when the chicken was observed with twisted neck and/or tremors.

Results:

25% of the birds died during the first 14 days. 5% of the birds suffered from neurological symptoms. Further, chicks infected with ERS 060E demonstrated an average weight of 442 grams at 21 days post-inoculation. Negative control birds had an average weight of 751 grams at 21 days post-inoculation.

Experiment 3i 20 broiler chickens were inoculated via the foot pad route with 0.2 ml at one day of age with strain ERS 074 ($10^2$ TCID$_{50}$/bird). The chickens were observed for clinical sign at 14 days.

TABLE 1

Percentage mortality

| Days after inoculation | Mortality (no. of birds) | % Mortality |
|---|---|---|
| 14 | 10 | 50 |

TABLE 2

Percentage neurological symptoms

| Days after inoculation | Neurological Symptoms (number birds)* | % NS |
|---|---|---|
| 14 | 1 | 5 |

*A chicken was determined to be showing neurological symptoms when the chicken was observed with twisted neck and/or tremors.

Results:

50% of the birds died during the first 14 days. 5% of the birds suffered from neurological symptoms. Further, chicks infected with ERS 074 demonstrated an average weight of 473 grams at 21 days post-inoculation. Negative control birds had an average weight of 751 grams at 21 days post-inoculation.

Experiment 3j

Experimental Design

Seventy-five SPF chickens and seventy-five commercial broilers with maternal antibodies against reovirus (MDA$^+$) were divided in 5 groups of 15 birds. The birds received plaque purified ERS strain isolate 1 orally or SC at 1 or 7 days of age. Table 1 shows the experimental design in detail. The chickens were observed daily for clinical sign during 7 weeks. At 7 weeks of age all remaining chickens were slaughtered.

TABLE 1

Experimental design

| Group | Immune status | Age of inoculation (days) | Route of inoculation | Dose ($\log_{10}$TCID$_{50}$/bird) |
|---|---|---|---|---|
| 1 | SPF | 1 | Oral | 5.2 |
| 2 | SPF | 1 | SC | 4.9 |
| 3 | MDA$^+$ | 1 | Oral | 5.2 |
| 4 | MDA$^+$ | 1 | SC | 4.9 |
| 5 | SPF | 7 | Oral | 4.9 |
| 6 | SPF | 7 | SC | 5.0 |
| 7 | MDA$^+$ | 7 | Oral | 4.9 |
| 8 | MDA$^+$ | 7 | SC | 5.0 |
| 9 | SPF | — | — | — |
| 10 | MDA$^+$ | — | — | — |

TABLE 2

Percentage mortality

| Group | Days after inoculation | Mortality (number birds) | % Mortality |
|---|---|---|---|
| 1 | 4-5 | 2 | 13.3 |
| 2 | 3-5 | 15 | 100 |
| 3 | 6-8 | 3 | 20 |
| 4 | 3-7 | 7 | 46.6 |
| 5 | — | 0 | 0 |
| 6 | — | 0 | 0 |
| 7 | — | 0 | 0 |
| 8 | — | 0 | 0 |
| 9 | — | 0 | 0 |
| 10 | — | 0 | 0 |

Results

Table 2 shows the percentage of birds that died after ERS inoculation. 100% of the SPF birds and 46.6% of the MDA$^+$ birds died after SC inoculation at 1 day of age within 3 to 7 days. The percentage mortality after oral inoculation at 1 day of age was 13.3 and 20% respectively for SPF and MDA$^+$ chickens within 4 to 8 days. When birds were inoculated at 7 days of age none of the birds died. Table 3 shows the percentage twisted necks. In both SPF and MDA$^+$ birds, neurological symptoms occur after oral or SC inoculation at 1 or 7 days of age. The neurological symptoms were seen from 6 days after inoculation.

TABLE 3

Percentage neurological symptoms

| Group | Days after inoculation | Neurological Symptoms (number birds/remaining birds) | % NS |
|---|---|---|---|
| 1 | — | 0 | 0 |
| 2 | — | 0 | 0 |
| 3 | 13 | 1/12 | 8.3 |
| 4 | 11 | 1/8 | 12.5 |
| 5 | — | 0 | 0 |
| 6 | 7 | 1/15 | 6.6 |
| 7 | 6-12 | 3/15 | 20 |
| 8 | — | 0 | 0 |
| 9 | — | 0 | 0 |
| 10 | — | 0 | 0 |

Experiment 3k

Experimental Design

Twenty-eight SPF chickens were inoculated SC at day old with 0.2 ml plaque purified strain ERS Poland 2 (4.6 $\log_{10} TCID_{50}$/birds). The chickens were observed daily for clinical signs during 14 days. At 14 days of age all chickens were slaughtered.

Results 96.4% of the chickens died during the first 6 days (Table 1). At day 9, one remaining chicken developed a twisted neck.

TABLE 1

| | Percentage mortality | |
|---|---|---|
| Days after infection | Mortality (number birds) | % Mortality |
| 3 | 10 | 35.7 |
| 4 | 15 | 89.3 |
| 5 | 1 | 92.8 |
| 6 | 1 | 96.4 |

Experiment 3l

Relatively Non-Pathogenic Strains

ERS strain 1037 was passed in embryonated eggs for approximately 10 passages to prepare a stock of virus that was used to inoculate 1-day old broiler chickens via the intratracheal route. A study of ERS strain 1037 was conducted against a highly pathogenic reovirus strain 1733.

Reo Strain 1037 Versus Reo Strain 1733

TABLE 1

| | | | Challenge results | | | |
|---|---|---|---|---|---|---|
| | | | 14 day challenge results | | | |
| Progeny Group | Chall. Strain | # chicks | # positive (weight)[1] | # positive (mortality)[2] | Total Positive | % Affected |
| SPF Controls | 1733 | 50 | 15 | 35 | 50 | 100 |
| | 1037 | 50 | 10 | 0 | 10 | 20 |

[1]Determined by t-test analysis
[2]Positive birds showed evidence of Reovirus infection at necropsy Strain 1037 was shown to be relatively non-pathogenic because only about 20% of the chickens were affected, exhibited any signs of malabsorption syndrome or growth depression, and none of the chickens died during the test period. This is in contrast to 1733, also a malabsorption virus, that caused 100% of the chickens to be affected, to have weight loss and/or death. Likewise, as can be seen, strain 1733 killed 35% percent of the chicks whereas strain 1037 killed none. Therefore, strain 1037 is relatively non-pathogenic, as herein defined.

Experiment 4

S1133 Infection of the Brains of Chickens After Oral Inoculation

Experimental Design:

10 SPF birds orally inoculated at day 1 with 2.6 $\log_{10}$/bird S1133 virus necropsy: 2 birds at 2, 3, 5, 7 and 10 dpc
isolation of reovirus from the brains using chickens embryo liver cells Result:

No isolation of reovirus from the brains at any time.

Conclusion:

S1133, a prior art strain, does not infect the brains of chickens after oral inoculation.

Experiment 5

Pathogenic Aspects of ERS Strains

Virus Strain

ERS 015 was isolated from commercial broilers from well-vaccinated parents in Poland in 1999. The birds suffered from high mortality and at necropsy white spots on liver and hydropericarditis were found. This isolate was identified as being a Reovirus using IFT. Further characterization with a panel of monoclonal antibodies confirmed that the isolate belonged to the ERS class. The isolate was plaque purified three times and will be used as the challenge strain in the efficacy studies. Preliminary experiments showed that ERS 015 isolate was able to produce tremor and twisted neck symptoms in 1-day old SPF birds. A pathogenesis study was conducted to confirm that the observed symptoms were caused by the new Reovirus strain.

Experimental Design

ERS 015 strain was plaque purified three times on CEF and used as challenge strain. One hundred and thirty-two 1-day-old SPF birds were divided in three groups. Group 1 had 55 birds and was inoculated intramuscularly with 0.2 ml of ERS 015 (1.0 $log_{10}$ $TCID_{50}$/bird) at day old. Group 2 had 55 birds and was inoculated orally with 0.2 ml of ERS 015 (2.0 $log_{10}$ $TCID_{50}$/bird) at day old. Group 3 had 22 birds and were inoculated intramuscularly with 0.2 ml PBS and served as negative control birds.

All chickens were observed daily for the occurrence of clinical symptoms of disease. Special attention was taken for neurological symptoms, as herein defined.

At 7, 14 and 21 days after inoculation, blood was taken from birds that were sacrificed. Serum samples were examined for the presence of antibodies against Reovirus strain ERS in the IFT, against Newcastle disease in the HI test, against infectious chickens encephalomyelitis virus (AEV) in the ELISA test and against Marek's disease in the ELISA.

Two or three birds of groups 1 and 2 and one bird of group 3 were sacrificed at 1, 2, 3, 4, 5, 6, 7, 10, 14, 17 and 21 days after challenge and examined for macroscopical lesions.

Samples of the brains were collected for virus isolation. The organs were placed in pycocrias tubes with glass beads and 1 ml of PBS+Pen strept (1000 μg U/ml). The mixtures were shaken for 20 minutes at the highest speed in a Retch mixer mill. After homogenisation 0.1 ml of the suspensions were inoculated on chicken embryo liver cells (CELi) ($1*10^6$ cells/ml in M6B8+0.1% NPPT+5% FCS). After 5 days incubation at 37° C. with 5% $CO_2$, all cultures were examined for specific REO CPE. If a suspension was negative a second inoculation on CEL was performed.

Samples of the brains, thoracic spinal cord, left and right sciatic nerves were collected for histological and immunohistochemical examination. Immunohistochemistry was performed for detection of reovirus antigen using monoclonal antibody 14-67 as primary antibody, a biotinylated secondary (rabbit-anti-mouse) antibody, streptavidin-biotine-enzyme-complex with alkaline phosphatase as enzyme, and new fuchsine as substrate.

Interpretation of the Results

Central nervous disorders were evaluated using the results of clinical symptoms, virus isolation and presence of viral antigen in the brains. If clinical symptoms were provoked by inoculation of ERS 015 and virus was present from the brains, ERS was indicated as a causative agent inducing central nervous disorders such as tremor and twisted neck.

Results

Clinical Symptoms

The results of the clinical signs of groups 1 and 2. No clinical signs were seen among birds of group 3. High mortality (80%) was seen within 7 days after IM inoculation while only one birds died at 10 days after oral inoculation. Poor growth and helicopter chickens were seen from day 4 and chickens stayed small until the end of the experiment in both groups. In both groups, 1 bird developed tremor and twisted neck at 9 or 10 days after IM or oral inoculation respectively.

TABLE 1

Clinical signs of birds in group 1.

| Days post inoculation | Mortality number/total | % | Helicopter chicken/ depressed/ poor growth number/total | % | Twisted neck Number/total | % |
|---|---|---|---|---|---|---|
| 1 | 0/55 | 0 | 0/55 | 0 | 0/55 | 0 |
| 2 | 0/52 | 0 | 0/52 | 0 | 0/52 | 0 |
| 3 | 0/49 | 0 | 0/49 | 0 | 0/49 | 0 |
| 4 | 2/46 | 4 | 46/46 | 100 | 0/46 | 0 |
| 5 | 15/41 | 37 | 41/41 | 100 | 0/41 | 0 |
| 6 | 8/23 | 35 | 23/23 | 100 | 0/23 | 0 |
| 7 | 1/12 | 8 | 12/12 | 100 | 0/12 | 0 |
| 8 | 0/8 | 0 | 8/8 | 100 | 0/8 | 0 |
| 9 | 0/8 | 0 | 8/8 | 100 | 1/8 | 13 |
| 10 | 0/8 | 0 | 8/8 | 100 | 1/8 | 13 |
| 11 | 0/6 | 0 | 6/6 | 100 | 0/6 | 0 |
| 12 | 0/6 | 0 | 6/6 | 100 | 0/6 | 0 |
| 13 | 0/6 | 0 | 6/6 | 100 | 0/6 | 0 |
| 14 | 0/6 | 0 | 6/6 | 100 | 0/6 | 0 |
| 15 | 0/4 | 0 | 4/4 | 100 | 0/6 | 0 |
| 16 | 0/4 | 0 | 4/4 | 100 | 0/4 | 0 |
| 17 | 0/4 | 0 | 4/4 | 100 | 0/4 | 0 |
| 18 | 0/2 | 0 | 2/2 | 100 | 0/2 | 0 |
| 19 | 0/2 | 0 | 2/2 | 100 | 0/2 | 0 |
| 20 | 0/2 | 0 | 2/2 | 100 | 0/2 | 0 |
| 21 | 0/2 | 0 | 2/2 | 100 | 0/2 | 0 |

TABLE 2

Clinical signs of birds in group 2.

| Days post inoculation | Mortality number/total | % | Helicopter chicken/ depressed/ poor growth number/total | % | Twisted neck number/total | % |
|---|---|---|---|---|---|---|
| 1 | 0/55 | 0 | 0/55 | 0 | 0/55 | 0 |
| 2 | 0/52 | 0 | 0/52 | 0 | 0/52 | 0 |
| 3 | 0/49 | 0 | 0/49 | 0 | 0/49 | 0 |
| 4 | 0/46 | 0 | 46/46 | 100 | 0/46 | 0 |
| 5 | 0/43 | 0 | 43/43 | 100 | 0/43 | 0 |
| 6 | 0/40 | 0 | 40/40 | 100 | 0/40 | 0 |
| 7 | 0/37 | 0 | 37/37 | 100 | 0/37 | 0 |
| 8 | 0/34 | 0 | 34/34 | 100 | 0/34 | 0 |
| 9 | 0/34 | 0 | 34/34 | 100 | 0/34 | 0 |
| 10 | 1/34 | 3 | 34/34 | 100 | 1/34 | 3 |
| 11 | 0/30 | 0 | 30/30 | 100 | 0/30 | 0 |
| 12 | 0/30 | 0 | 30/30 | 100 | 0/30 | 0 |
| 13 | 0/30 | 0 | 30/30 | 100 | 0/30 | 0 |
| 14 | 0/30 | 0 | 30/30 | 100 | 0/30 | 0 |
| 15 | 0/27 | 0 | 27/27 | 100 | 0/27 | 0 |
| 16 | 0/27 | 0 | 27/27 | 100 | 0/27 | 0 |
| 17 | 0/27 | 0 | 27/27 | 100 | 0/27 | 0 |
| 18 | 0/24 | 0 | 24/24 | 100 | 0/24 | 0 |
| 19 | 0/24 | 0 | 24/24 | 100 | 0/24 | 0 |
| 20 | 0/24 | 0 | 24/24 | 100 | 0/24 | 0 |
| 21 | 0/24 | 0 | 24/24 | 100 | 0/24 | 0 |

Serology

No antibodies were found in negative control group and no antibodies against NDV, Marek's disease and AEV were found in the examined chickens. Antibody titres against ERS were <2.0, 5.0, and 7.0 $\log_2$ at 7, 14 and 21 days of age respectively when inoculated IM and orally.

Macroscopic and Microscopic Examination

The results of the macroscopic lesions found in different organs of chickens of group 1 and 2 are shown in Tables 1 and 2, respectively. No macroscopic abnormalities were found in birds of groups 3. In groups 1 and 2, lesions were found in the liver (enlarged with multiple white to yellow foci), in the spleen (enlarged, hard consistence with discoloration), hydropericard, brains (large haemorrhage on the back of the cerebrum, atrophic). In group 1 lesions were also found in the leg muscle and tendon (swollen with oedema).

Microscopic examination: in the sciatic nerve a finding (apparently) related to reovirus infection was a (multi) focal inflammation with mononuclear or mixed infiltration, presence of fibroblasts, degeneration of collagen fibres, with or without small foci of necrosis. This inflammation was predominantly observed in adjacent (or surrounding/interstitial/intercalating) connective tissue in few cases extending into the sciatic nerve tissue itself. Furthermore, mononuclear or heterophilic infiltration was observed and might be related to reovirus infection. In the spinal cord 3 animals with suspected satellitosis were found. In the connective tissue of the spinal ganglion adjacent to the spinal ganglion (or in the area of the spinal ganglion without evidence of it) an inflammation was observed comparable to that in sciatic nerve. Secondly, foci of mononuclear infiltration within the spinal ganglion were observed that might also be glial cell aggregates, and also regarded as related to reovirus infection. In the sciatic nerve (central part), in only one animal an inflammation of adjacent connective tissue as seen in the peripheral sciatic nerve. In a small number of animals mononuclear infiltration in the connective tissue was observed. In the brain several findings were observed including 1 foci of gliosis or perivascular mononuclear infiltration, congestion of Plexus chorioideus loops with or without presence of infiltrates.

IHC was done on the right sciatic nerve, abdominal spinal cord and brains of birds from group 1 and on the abdominal spinal cord and brains of birds of group 2. Positive IHC was marked as cases of infiltration/inflammation in connective tissue. Except in one animal of group 1 at 7 dpc a ganglion cell was found positive for viral antigen. In the brains the plexus choroideus cells or related cells became positive from day 4 till 7 in group 1 and from day 5 till 7 in group 2.

TABLE 1

Macroscopic lesions in different organs of birds of group 1.

| Days post inoculation | Liver | Spleen | hydropericard | Leg muscle/ Hock joint | Brains |
|---|---|---|---|---|---|
| 1 | 0/3* | 0/3 | 0/3 | 0/3 | 0/3 |
| 2 | 0/3 | 0/3 | 0/3 | 0/3 | 0/3 |
| 3 | 3/3 | 3/3 | 0/3 | 0/3 | 0/3 |
| 4 | 3/3 | 3/3 | 0/3 | 0/3 | 0/3 |
| 5 | 3/3 | 3/3 | 0/3 | 0/3 | 0/3 |
| 6 | 3/3 | 3/3 | 0/3 | 3/3 | 2/3 |
| 7 | 2/3 | 3/3 | 1/3 | 0/3 | 2/3 |
| 10 | 2/2 | 2/2 | 2/2 | 2/2 | 2/2 |
| 14 | 0/2 | 0/2 | 2/2 | 0/2 | 0/2 |
| 17 | 2/2 | 0/2 | 1/2 | 1/2 | 0/2 |
| 21 | 1/2 | 0/2 | 2/2 | 2/2 | 0/2 |

*Number of positive birds/total number of birds

TABLE 2

Macroscopic lesions in different organs of birds of group 2.

| Days post Inoculation | Liver | Spleen | Hydropericard | Leg muscle/ Hock joint | Brains |
|---|---|---|---|---|---|
| 1 | 0/3* | 0/3 | 0/3 | 0/3 | 0/3 |
| 2 | 0/3 | 0/3 | 0/3 | 0/3 | 0/3 |
| 3 | 3/3 | 2/3 | 0/3 | 0/3 | 0/3 |
| 4 | 1/3 | 3/3 | 0/3 | 0/3 | 0/3 |
| 5 | 1/3 | 1/3 | 0/3 | 0/3 | 0/3 |
| 6 | 3/3 | 3/3 | 0/3 | 0/3 | 2/3 |
| 7 | 3/3 | 3/3 | 0/3 | 0/3 | 2/3 |
| 10 | 3/3 | 2/3 | 1/3 | 0/3 | 0/3 |
| 14 | 3/3 | 2/3 | 2/3 | 0/3 | 0/3 |
| 17 | 1/3 | 2/3 | 1/3 | 0/3 | 0/3 |
| 21 | 0/3 | 0/3 | 0/3 | 0/3 | 0/3 |

*Number of positive birds/total number of birds

Isolation of Reovirus

The results of Reovirus isolation from different organs of birds of groups 1 and 2 are demonstrated in Tables 3a and 3b respectively. No virus was isolated from chickens of group 3. Reovirus was detected in all organs of chickens of group 1 and 2. After IM or oral inoculation isolation of virus started from 1 or 2 days after inoculation respectively. In both groups the brains were positive till 10 days after inoculation and the tendon stayed positive until 21 days after inoculation.

Discussion

This report describes the pathogenesis of ERS 015 in order to reveal the pathway of ERS infecting the central nervous system. Two inoculation routes were used, IM and orally. In both cases ERS 015 was able to induce a twisted neck in one bird at 9 or 10 days after inoculation. These neurological symptoms can be related to the presence of virus in the brains. ERS 015 was isolated from the brains from all examined chickens from day 1 or 2 days after inoculation. Also viral antigen was demonstrated in the brains.

Histological evaluation indicates, that after IM inoculation, spread of reovirus occurs more rapidly (lesions are seen earlier in several organs) and more effectively (lesions are observed during a longer time period) than after oral inoculation. Furthermore it was indicated, that nerve tissue (peripheral sciatic nerve or the surrounding connective tissue) might be a target tissue for reovirus infection with the strain ERS. Histological findings suggest, that spread of reovirus to the brain occurs via the hematogenous route rather than along nerve fibers.

To our knowledge this is the first time that an avian Reovirus isolate is capable of causing central nervous system disorders.

TABLE 3a

Isolation of ERS 015 from different organs of chickens of group 1.

| Days post inoculation | Isolation of ERS 015 from | | | | |
|---|---|---|---|---|---|
| | Brains | Leg muscle | Hock joint | Liver | Spleen |
| 1 | 0/3* | 2/3 | 0/3 | 2/3 | 0/3 |
| 2 | 2/3 | 3/3 | 1/3 | 3/3 | 3/3 |
| 3 | 3/3 | 3/3 | 3/3 | 3/3 | 3/3 |
| 4 | 3/3 | 3/3 | 3/3 | 3/3 | 3/3 |
| 5 | 3/3 | 3/3 | 3/3 | 3/3 | 3/3 |
| 6 | 3/3 | 3/3 | 3/3 | 3/3 | 3/3 |
| 7 | 3/3 | 3/3 | 3/3 | 3/3 | 3/3 |
| 10 | 2/2 | 2/2 | 2/2 | 2/2 | 2/2 |
| 14 | 1/2 | 2/2 | 2/2 | 1/2 | 2/2 |
| 17 | 0/2 | 0/2 | 2/2 | 1/2 | 2/2 |
| 21 | 0/2 | 0/2 | 2/2 | 2/2 | 1/2 |

TABLE 3b

Isolation of ERS 015 from different organs of chickens of group 2.

| Days post inoculation | Isolation of ERS 015 from | | | | |
|---|---|---|---|---|---|
| | Brains | Leg muscle | Hock joint | Liver | Spleen |
| 1 | 0/3* | 0/3 | 0/3 | 0/3 | 0/3 |
| 2 | 0/3 | 0/3 | 0/3 | 0/3 | 0/3 |
| 3 | 1/3 | 2/3 | 3/3 | 2/3 | 2/3 |
| 4 | 1/3 | 2/3 | 2/3 | 2/3 | 2/3 |
| 5 | 2/3 | 3/3 | 3/3 | 3/3 | 3/3 |
| 6 | 3/3 | 3/3 | 3/3 | 3/3 | 3/3 |
| 7 | 3/3 | 3/3 | 3/3 | 3/3 | 3/3 |
| 10 | 3/3 | 3/3 | 3/3 | 3/3 | 3/3 |
| 14 | 0/3 | 1/3 | 3/3 | 3/3 | 3/3 |
| 17 | 0/3 | 2/3 | 3/3 | 3/3 | 3/3 |
| 21 | 0/2 | 0/2 | 2/2 | 0/2 | 0/2 |

*Number of positive birds/total number of birds

Experiment 6

Protection against ERS 015 Challenge of Progeny from Layers Vaccinated with Inactivated Vaccine Containing ERS Objective The aim of the present study was to assess the level of protection against ERS 015 challenge of progeny from layers vaccinated with inactivated vaccine containing ERS. The efficacy claim protection against central nervous disorders was evaluated in this experiment.

Experimental Design

Eggs, derived from SPF-layers that were not vaccinated or vaccinated with inactivated ERS vaccine, were collected and hatched. Forty chicks (designated group 1) from layers vaccinated with ERS and forty chicks (designated group 2) from layers not vaccinated with ERS (180 EU/dose) were orally challenged with 0.2 ml ERS 015 (2.0 $\log_{10}$ $TCID_{50}$/bird) at day old. Eight chicks (designated group 3) from layers not vaccinated with ERS were inoculated with 0.2 ml PBS orally and IM.

All chickens were observed daily for the occurrence of clinical signs of disease according to standard procedures. Special attention was taken for central nervous disorders such as tremor and twisted neck Five chickens of groups 1 and 2 and 1 chicken of group 3 were sacrificed at 3, 7, 10, 14, 21, 28, 35 and 42 days after challenge. Samples of the brains were collected for virus isolation. The same procedure was followed as described in experiment 5.

Interpretation of the Results

Protection against neurological symptoms was evaluated using the results of virus isolation for the brains. The progeny was considered protected when a significant reduction in virus replication was shown in the brains of progeny from vaccinated layers compared to progeny from non-vaccinated layers.

Results

Clinical Symptoms

No clinical signs were seen among birds of group 3. Mortality was seen in group 1 (5 birds) and group 2 (9 birds). At necropsy enlarge liver with multiple white spots, enlarged spleens and or hydropericard that could be related to reovirus infection were found in 2 of the 5 birds of group 1 and in 8 of the 9 birds of group 2. Twisted neck was seen in one bird of group 1 at 14 dpc.

Isolation of Reovirus

The results of Reovirus isolation after 2 passages from the brains of birds are shown in Table 1. Due to the number of dead birds in groups 1 and 2 it was decided to kill less birds (3 or 4) at certain necropsy dates. No virus was isolated from the brains of chickens of group 1 and 3. In group 2 the brains were positive till 14 days after inoculation.

TABLE 1

Isolation of ERS 015 from the brains.

| Days post inoculation | Isolation of ERS 015 from group | | |
|---|---|---|---|
| | 1 | 2 | 3 |
| 3 | 0/5* | 5/5 | 0/5 |
| 7 | 0/4 | 4/4 | 0/5 |
| 10 | 0/4 | 3/3 | 0/5 |
| 14 | 0/4 | 0/3 | 0/5 |
| 21 | 0/4 | 0/3 | 0/5 |
| 28 | 0/4 | 0/4 | 0/5 |
| 35 | 0/5 | 0/4 | 0/5 |
| 42 | 0/5 | 0/5 | 0/5 |

*Number of positive birds/total number of birds

Discussion

This experiment describes the efficacy of an ERS inactivated vaccine against CNS disorders. It is clear that vaccination of the layers with inactivated ERS vaccine protect the progeny of an ERS infection. Mortality was lower in the birds with maternal antibodies. Only 2 birds compare to 8 birds in the group without antibodies died from ERS infection. Furthermore none of the birds with maternal antibodies had virus in the brains, while all birds of group 2 were positive till 14 dpc. One chicken had a twisted neck in group 1 possibly a result of a vaccine with too low amount of antigenic mass of ERS. No CNS was seen in group 2 but on the other hand, 9 of the 40 birds died within 13 dpc and this is the time that twisted necks can be developed. It could be that those chickens past away before nervous symptoms could appear. It can be concluded based on mortality and ERS isolation from the brains that anti-ERS maternal antibodies protect the progeny from CNS disorders caused by ERS.

For a further understanding of the scope of the present invention, consideration should be had to the appended Claims.

What we claim is:

1. A method for protecting poultry from neurological symptoms caused by avian reovirus, comprising administering an effective amount of an immunogenic composition comprising an avian reovirus, wherein the avian reovirus is selected from the group consisting of strain ERS 060E (ATCC Deposit number PTA-4782), strain ERS 074 (ATCC Deposit number PTA-4783), and strain ERS 1037 (ATCC Deposit number PTA-4735), and wherein the poultry is selected from the group consisting of chickens, turkeys, water fowl, guineas, quail, pigeons, and ostriches.

2. The method of claim 1, wherein the reovirus is in a live, attenuated or killed form.

3. The method of claim 1, wherein the immunogenic composition further comprises a vaccine strain of at least one of Marek's Disease Virus, Infectious Bursal Disease Virus, Newcastle Disease Virus, Infectious Bronchitis Virus, Avian Encephalomyelitis Virus, Fowl Pox Virus, and Chicken Anemia Agent.

4. The method of claim 1, wherein the immunogenic composition further comprises an adjuvant.

5. The method of claim 1, wherein the neurological symptoms are selected from the group consisting of tremors and twisted neck.

* * * * *